United States Patent [19]
Laitinen et al.

[11] Patent Number: 6,087,507
[45] Date of Patent: Jul. 11, 2000

[54] SEPARATION OF PYRIDINE OR PYRIDINE DERIVATIVES FROM AQUEOUS SOLUTIONS

[75] Inventors: Antero Laitinen, Helsinki; Marko Maukonen, Kuusankoski, both of Finland

[73] Assignee: Valtion Teknillinen Tutkimuskeskus, Espoo, Finland

[21] Appl. No.: 09/297,135

[22] PCT Filed: Oct. 24, 1997

[86] PCT No.: PCT/FI97/00645

§ 371 Date: Apr. 26, 1999

§ 102(e) Date: Apr. 26, 1999

[87] PCT Pub. No.: WO98/18744

PCT Pub. Date: May 7, 1998

[30] Foreign Application Priority Data

Oct. 30, 1996 [FI] Finland ................................ 964369

[51] Int. Cl.[7] .................................................. C07D 211/70
[52] U.S. Cl. ............................................ 546/353; 546/348
[58] Field of Search .................................... 546/353, 348

[56] References Cited

U.S. PATENT DOCUMENTS

| 4,349,415 | 9/1982 | DeFilippi et al. | 203/14 |
| 5,100,514 | 3/1992 | Berg et al. | 203/14 |
| 5,116,508 | 5/1992 | Kumar et al. | 210/639 |

FOREIGN PATENT DOCUMENTS 0281464  9/1988  European Pat. Off. .

OTHER PUBLICATIONS

Chemical Abstracts 109:204133, abstract of Ashraf–Khorassani, 1988.
Thomas G. Squires et al., FUEL, vol. 61, Nov. 1982, pp. 1170–1172.
Shimizu et al., Pyridine and Pyridine Derivatives, in Ullman's Encyclopedia of Industrial Chemistry, 5th ed., vol. A22, p. 403.
M. McHugh, V. Krukonis, Supercritical Fluid Extraction, 2nd ed., Butterworth–Heinemann, 1994, pp. 170–188.
J.L. Hedrick et al., J. of High Res. Chrom., vol. 5, Mar. 1992, pp. 151–154.
Fuel, vol. 61, Nov. 1982, Thomas G. Squires et al., pp. 1170–1172.
M. Ashraf–Khorassani and L.T. Taylor, Chromatographic Behavior of Polar Compounds With Liquid vs. Supercritical Fluid Mobile Phases, *Journal of Chromotographic Science*, vol. 26, Jul. 1988, pp. 331–336.

*Primary Examiner*—D. Margaret Seaman

[57] ABSTRACT

The present invention relates to a method of continuously separating pyridine or pyridine derivatives from aqueous solutions by extraction, wherein supercritical fluid is employed to extract the pyridine material from liquid media. The method of the invention, in particular, extracts pyridine or pyridine derivatives from aqueous solutions with pressurized carbon dioxide, which is used under pressure, or in the liquid state, or in the near critical state or in the supercritical state. The operating system is a continuously operating extraction system, so that a part, or all, of the pyridine and/or pyridine derivatives are transferred from the aqueous phase to the carbon dioxide phase, and thereafter the aqueous phase and carbon dioxide phase are separated from each other; and the pyridine and/or pyridine derivatives are separated from carbon dioxide; and the extract containing pyridine and/or pyridine derivatives is thereby obtained. Preferred temperatures for the pyridine and/or pyridine derivative contacting with carbon dioxide are from 5 to 80° C.; and preferred pressures range from 60 to 300 bar. Specific pyridine derivatives which are usefully separated comprise alkylpyridine, vinylpyridine or halopyridine. In the operating system according to the invention the carbon dioxide is preferentially recycled back to the extraction system in a preferred embodiment.

6 Claims, 1 Drawing Sheet

SEPARATION OF PYRIDINE OR PYRIDINE DERIVATIVES FROM AQUEOUS SOLUTIONS

This application is the national phase under 35 U.S.C. §371 of PCT International Application No. PCT/FI97/00645 which has an International filing date of Oct. 24, 1997 which designated the United States of America.

TECHNICAL FIELD OF THE INVENTION

The present invention concerns a method in accordance with the preamble of claim 1 for separation of pyridine or pyridine derivatives from aqueous solutions by extraction.

BACKGROUND OF THE INVENTION

Pyridine, $C_5H_5N$, is a six-membered heterocyclic compound containing one nitrogen atom. Pyridine is miscible in all proportions with water and its boiling point is 115.3° C. Pyridine forms an azeotrope with water at 93.6° C., containing 41 wt-% water. Pyridine derivatives are for example alkylpyridines, vinylpyridines, halopyridines, aminopyridines, pyridinols and pyridyl alcohols. Alkylpyridines are for example 2-methylpyridine, 3-methylpyridine, 4-methylpyridine, 2.6-dimethylipyridine, 3.5-dimethylipyridine and 2-ethyl-2-methylipyridine. Pyridine and pyridine derivatives are used as starting material for pharmaceutical and agrochemicals. Pyridine compounds are also used as a solvent and as catalysts.

The reaction of aldehydes or ketones with ammonia is the most general industrial synthetic reaction for the manufacture of pyridine bases. The reaction is usually carried out at 350–500° C. and atmospheric pressure in the presence of a catalyst. A schematic flow sheet of pyridine and methylpyridine production is presented in literature[1]. Ammonia, acetaldehyde and formaldehyde are fed to a catalyst containing reactor, where pyridine, alkylpyridine, water and hydrogen are formed. The reaction mixture is separated from ammonia and hydrogen by a collector, after which pyridine and methylpyridines are extracted from aqueous solution with suitable solvent, e.g. with benzene. The solvent is separated from the pyridines by distillation and recycled to the extraction column. Pyridine and alkylpyridines are isolated in continuous distillation columns.

Pyridine or pyridine derivative containing waste waters are formed in the industry. Because pyridine is very bioactive, it must be removed from water with a suitable method.

It is known that hydrocarbons and oxygenated hydrocarbons, such as alcohols, esters, organic acids, aldehydes, ketones or phenols, can be extracted from aqueous solutions by using near-critical or supercritical state solvent, such as carbon dioxide, ethane or ethene (U.S. Pat. No. 4,349,415). It is also known that the extraction of dioxane, acetone, formamide. N.N-dimethylformamide and ethyleneglycol have been tried[2]. The above mentioned compounds are neutral or acidic, and there is no acid-base interaction between the solvent and the solute.

It is difficult to extract nitrogen containing organic compounds from water with carbon dioxide for two reasons. First, many of the nitrogen containing compounds are very soluble in water, and the distribution coefficient is very low. For example, the distribution coefficient of formamide in $CO_2$-water formamide systems is only 0.001 (weight bases), which is too small to allow effective extraction[3]. Second, the pH of water will decrease to approximately 3.5 as high density carbon dioxide is introduced, and any reasonably basic compound will protonate, increasing its solubility in water and decreasing solubility in carbon dioxide. Protonated compounds are not expected to be extractable with non-polar carbon dioxide solvent. Further, if the compound is a strong base, it will react with acidic carbon dioxide. It is known from the literature that 2.5-dimethylpyridine has been tried to extract from water with supercritical carbon dioxide[4]. In these experiments 2.5-dimethylpyridine could not be extracted from dilute aqueous solution with supercritical carbon dioxide.

DESCRIPTION OF THE INVENTION

The present invention is based upon the discovery that heterocyclic aromatic bases, such as pyridine and/or pyridine derivatives can be extracted almost quantitatively from aqueous solutions with liquid, near-critical or supercritical carbon dioxide. The measured distribution coefficients indicate that pressurized carbon dioxide is an excellent solvent for the extraction of pyridine from aqueous solutions. The invention is based on the insight that carbon dioxide is a weak acid and pyridine and/or pyridine derivatives are weak bases. The acid-base interaction between the solute and the solvent makes carbon dioxide a particularly suitable solvent for the extraction of certain weak bases from aqueous solutions.

The word supercritical refers to the state of the solvent. For example carbon dioxide is at supercritical state when its temperature is above 31.1° C. and simultaneously the pressure is above 73.8 bar. Corresponding values for ethane are 32.4° C. and 48 bar, and for propane 96.8° C. and 42 bar. Supercritical fluids exhibit both liquid- and gas-like properties, such as liquid-like density and gas-like viscosity. The diffusivity of supercritical fluids is between the values of gases and liquids. Gas-like properties are considered to be beneficial in extraction due to enhanced mass transfer. Carbon dioxide is environmentally acceptable, non-toxic, non-flammable, non-corrosive and easily available. Further, carbon dioxide is the second least expensive solvent after water.

This invention makes possible the construction of more simple and more efficient extraction processes for separation of pyridine and/or pyridine derivatives from aqueous solutions. In conventional liquid-liquid extraction processes, the separation of solvent from solute is usually carried out by distillation, which is a a very energy intensive operation. The supercritical solvent, being usually a pressurized gas at NTP, can be relatively easily and economically separated from the product by depressurising the solvent mixture and evaporating the supercritical solvent. The heat of vaporization of carbon dioxide is low compared to organic liquid solvents. The simplified solvent recycling means savings in energy costs. Further, flammable or harmful solvents used in traditional liquid-liquid extraction processes can be replaced by environmentally acceptable carbon dioxide.

DETAILED DESCRIPTION

Figure 1:
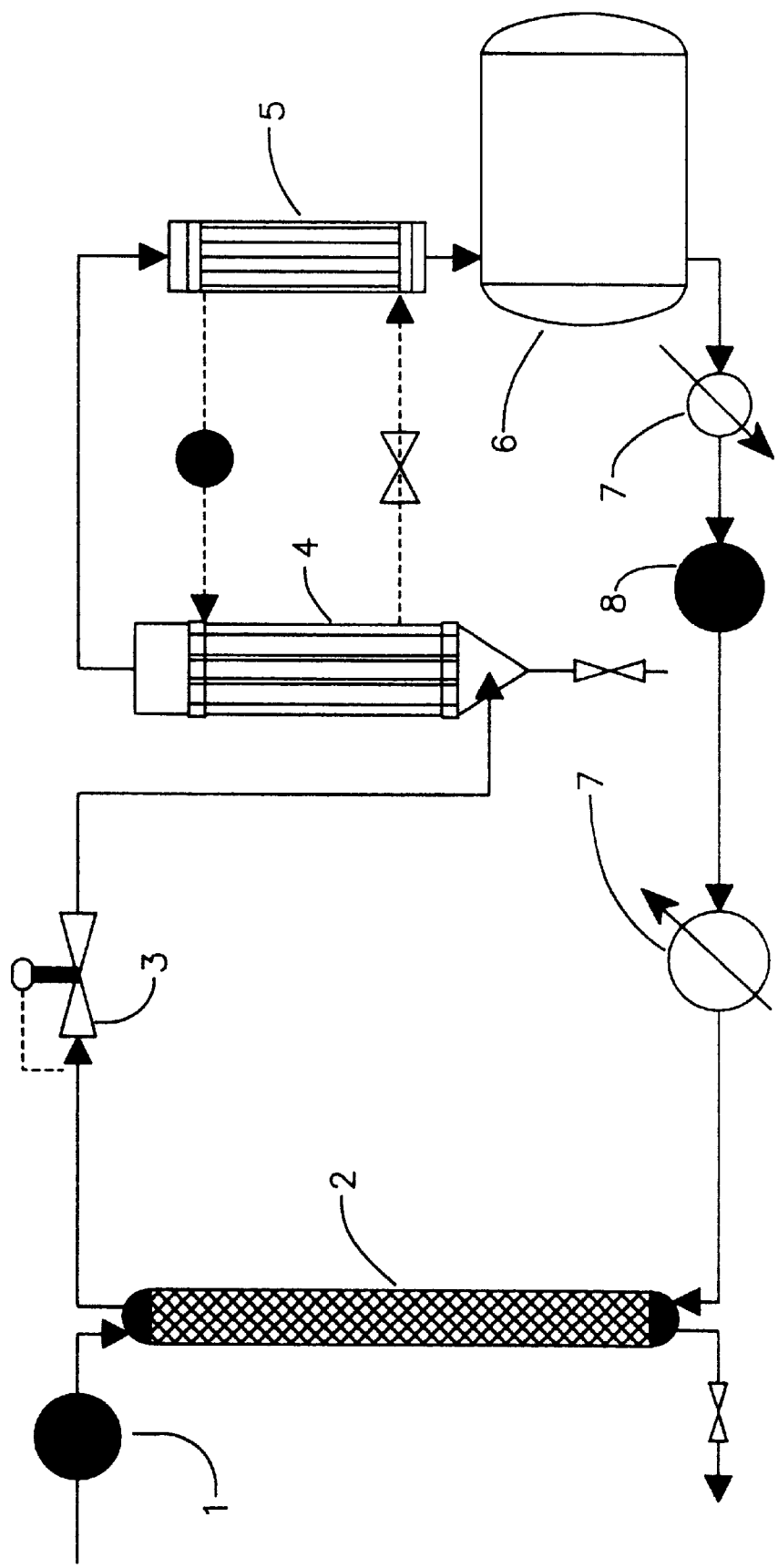

The extraction can be carried out in any kind of apparatus, where aqueous pyridine and/or pyridine derivatives containing solution is contacted with carbon dioxide solvent, but obviously continuous extraction systems are preferable in industrial practice.

In FIG. 1 is presented a typical installation for high pressure extraction in accordance with the invention. Aqueous pyridine and/or pyridine derivative containing solution is continuously pumped (1) to the top of the extraction column (2). The aqueous pyridine and/or pyridine containing solution can be a complex mixture of several organic or inorganic compounds. Pressurized carbon dioxide solvent is pumped to the bottom of the column. Aqueous phase is more dense than the carbon dioxide phase, and it flows downwards in the column. Whereas the carbon dioxide phase flows upwards in the column. When the phases are contacted in the column, pyridine and/or pyridine derivates are transferred from the aqueous phase to the carbon dioxide phase. The raffinate coming out from the bottom of the column is almost pure water, whereas the extract contains pyridine and/or pyridine derivatives and carbon dioxide. Different types of columns can be used, e.g. spray, packed, sieve tray or mechanically agitated extraction column.

Pyridine and/or pyridine derivatives are separated from the carbon dioxide solvent by reducing the pressure (3) in the specific separation vessel (4). Part of carbon dioxide is liquefied as a consequence of the pressure reduction, and it is evaporated. The heat of vaporization of carbon dioxide is almost ten times less than for example the heat of vaporization of toluene. The evaporated carbon dioxide is condensed in the condenser (5) and collected in the container (6), after which it can be pumped (8) through the heat exchangers (7) back to the extraction column (2).

The presented example is only one possible technical application in accordance with the invention, and other process and equipment solution are possible. For example other possible methods to separate pyridine and/or pyridine derivatives from carbon dioxide solvent are membrane separation, washing with suitable solvent and changing the temperature of the extract mixture.

It is well known, that modifiers or entrainers can be used to enhance the pyridine and/or pyridine derivative extraction from aqueous solutions. These modifies include for example alcohols, esters, aldehydes, ketones and other related hydrocarbons.

The technical feasibility of extraction can be described with the aid of distribution coefficient. In dilute systems the distribution coefficient K can be written as $$K = \frac{y^*}{x^*} \quad (1)$$

where $y^*$ is the concentration of the solute in the solvent phase at equilibrium, and $x^*$ is the concentration of the solute in the aqueous phase at equilibrium. The higher the K-value, the better is the solvent for the selected application. For example the distribution coefficient of ethanol in dilute ethanol-$CO_2$-water system is approximately 0.09 (weight bases).

The invention is described in detail in the following with the aid of embodiment experiments.

EXAMPLE 1

Measurement of Distribution Coefficients

Distribution coefficients of pyridine in pyridine-$CO_2$-water system were measured in a 30 mL pressure vessel, which was equipped with a movable piston and sapphire window to allow visual observation. Aqueous pyridine containing solution was first loaded to the vessel. The total amount of the solution and the initial pyridine concentration in the solution were known. The pressure vessel was heated to the desired temperature, after which the vessel was pressurized with carbon dioxide according the procedure which allowed the determination of the loaded carbon dioxide. The desired pressure inside the vessel was reached by moving the piston with the assistance of the hydraulic unit. After the desired temperature and pressure were reached magnetic stirrer was turned on. The solution was mixed 4 to 5 hours, after which the magnetic stirrer was turned of. During the experiment part of the pyridine dissolved to the carbon dioxide phase, whereas part of it remained in the aqueous phase. After one hour a sample was taken from the aqueous phase simultaneously holding the constant pressure inside the vessel. Pyridine concentration in the sample was analyzed by gas chromatography (GC). The value of distribution coefficient in each experiment was calculated on the bases of the initial and final pyridine concentrations in the aqueous phase and the amounts of aqueous and carbon dioxide phases. The results are seen in Table 1.

EXAMPLE 2

Extraction of Pyridine and Pyridine Derivatives in a Semi-batch System 30 mL aqueous solution, which contained 5 wt-% pyridine, 1 wt-% vinylpyridine and 0.5 wt-% 2-chloropyridine was closed to a 100 mL pressure vessel, and the vessel was heated to the extraction temperature and pressurized with carbon dioxide. Carbon dioxide (100 bar, 40° C.) was pumped through the aqueous phase. The flow rate of carbon dioxide was approximately 1 kg/h. After 30 minutes extraction the pressure vessel was depressurized and opened. The pyridine and pyridine derivative concentrations in the aqueous solution after extraction were analyzed with gas chromatography (Perkin-Elmer 900). The pyridine concentration in the aqueous phase was less than 0.2 wt-%. The aqueous solution did not any more contain significant amounts of vinylpyridine or 2-chloropyridine.

EXAMPLE 3

Extraction of Pyridine in a Semi-batch System

Using procedures similar to example 2, aqueous solution containing initially 65 wt-% pyridine was extracted with supercritical carbon dioxide (100 bar, 35° C.). After 60 minutes extraction pyridine concentration in the aqueous phase was less than 0.5 wt-%.

EXAMPLE 4

Extraction of Pyridine in a Semi-bat

Using procedures similar to example 2, aqueous solution containing initially 0.1 wt-% pyridine was extracted with supercritical carbon dioxide (100 bar, 35° C.). After 60 minutes extraction pyridine concentration in the aqueous phase was less than 0.002 wt-%.

EXAMPLE 5

Extraction of Pyridine in a Continuous System

Aqueous solution, containing initially 10 wt-% pyridine, was extracted in a continuous mechanically agitated column with supercritical carbon dioxide (100 bar, 40° C.). The height of the column was 2 m and the diameter of the column was 35 mm. Aqueous pyridine solution was pumped to the top of the column, and the flow rate was approximately 2 kg/h. Carbon dioxide was pumped to the bottom of the column, and the flow rate was approximately 10 kg/h. After the equilibrium was reached in the column, samples were taken from the raffinate. Samples were analyzed chromatographically with Perkin-Elmer 900 gas chromatograph equipped with Porapak Q column. Pyridine concentration in the raffinate phase was less than 0.3 wt-%. The extract contained approximately 90 wt-% pyridine.

EXAMPLE 6

Extraction of Pyridine in a Continuous System

Using procedures similar to example 5, aqueous solution containing initially 15 wt-% pyridine was extracted with liquid carbon dioxide (200 bar, 25° C.). After extraction the pyridine concentration in the raffinate was less than 0.3 wt-%.

EXAMPLE 7

Extraction of Pyridine in a Continuous System

Using procedures similar to example 5, aqueous solution containing initially 15 wt-% pyridine was extracted with supercritical carbon dioxide (300 bar, 80° C.). The flow rate of carbon dioxide was approximately 4 kg/h. After extraction the pyridine concentration in the raffinate was less than 1 wt-%.

EXAMPLE 8

Extraction of Pyridine and Pyridine Derivatives in a Continuous System

Using procedures similar to example 5, aqueous solution containing initially 5 wt-% pyridine, 2 wt-% 3-methylpyridine, and 0.5 wt-% 5-ethyl-2-methylpyridine was extracted from aqueous solution with supercritical carbon dioxide (150 bar, 50° C.). After extraction the raffinate was analyzed. The concentration of pyridine in the raffinate was less than 0.04 wt-% and the concentration of the alkylpyridines were less than 0.06 wt-%.

EXAMPLE 9

Extraction of Pyridine and Pyridine Derivatives in a Continuous System

Using procedures similar to example 5, aqueous solution initially containing 3 wt-% pyridine, 1 wt-% 3-methyl pyridine, and 1 wt-% 2.6-dimethylpyridine was extracted with liquid carbon dioxide (60 bar, 5° C.). After extraction the concentrations of pyridine and pyridine derivatives in the aqueous phase were less than 0.1 wt-%.

TABLE 1

Pyridine distribution coefficients (K-value) in pyridine-$CO_2$-water system.

| No. | Conditions | Initial pyridine concentration in aqueous phase wt-% | Final pyridine concentration in aqueous phase wt-% | K-value |
|---|---|---|---|---|
| 1 | 100 bar/25° C. | 3.0 | 0.32 | 4.12 |
| 2 |  | 10.0 | 1.33 | 2.94 |
| 3 |  | 20.0 | 6.13 | 1.04 |
| 4 | 100 bar/45° C. | 3.0 | 0.45 | 3.81 |
| 5 |  | 10.0 | 2.87 | 1.4 |
| 6 |  | 20.0 | 9.81 | 0.58 |
| 7 | 200 bar/45° C. | 3.0 | 0.29 | 5.08 |
| 8 |  | 10.0 | 1.82 | 2.78 |
| 9 |  | 20.0 | 5.84 | 1.43 |

REFERENCES

Shimizu et al. Pyridine and pyridine derivatives, in *Ullman's Encyclopedia of Industrial Chemistry*, 5th ed., vol. A22, page 403.

M. McHugh V. Krukonis, Supercritical Fluid Extraction, 2nd ed., Butterworth-Heinemann, 1994, pp 170–188.

M. McHugh, V. Krukonis, *Supercritical Fluid Extraction*, 2nd ed., Butterworth-Heinemann, 1994, p 182.

J. L. Hedrick, L. T. Taylor, Direct Supercritical Fluid Extraction of Nitrogen Bases from Aqueous Solutions, *J of High Res. Chrom.*, vol. Mar. 15, 1992, pp 151–154).

What is claimed is:

1. A method of continuously separating pyridine and/or pyridine derivatives from aqueous solutions by extraction, comprising the steps of:

(a) contacting an aqueous solution containing pyridine and/or pyridine derivatives with pressurized or near-critical or supercritical carbon dioxide in a continuously operating extraction system so that a part or all of the pyridine and/or pyridine derivatives are transferred from an aqueous phase to a carbon dioxide phase;

(b) separating the aqueous phase and the carbon dioxide phase from each other; and (c) separating pyridine and/or pyridine derivatives from carbon dioxide, whereupon the extract containing pyridine and/or pyridine derivatives is obtained.

2. The method according to claim 1, wherein pyridine and/or a pyridine derivative is contacted with carbon dioxide at temperatures from 5 to 80° C. and at pressures from 60 to 300 bar.

3. A method according to claim 1, wherein said pyridine derivative is alkylpyridine, or vinylpyridine or halopyridine.

4. A method according to claim 1, wherein the carbon dioxide is preferentially recycled back to the extraction system.

5. The method according to claim 1, wherein extraction is conducted in a continuous mechanically agitated column.

6. The method of claim 1, wherein extraction is performed in a spray, packed or sieve tray column.

* * * * *